United States Patent [19]
Rattner

[11] Patent Number: 5,301,660
[45] Date of Patent: Apr. 12, 1994

[54] THERAPY APPARATUS FOR TREATING A SUBJECT WITH FOCUSED ACOUSTIC WAVES

[75] Inventor: Manfred Rattner, Grossenseebach, Fed. Rep. of Germany

[73] Assignee: Siemens Aktiengesellschaft, Munich, Fed. Rep. of Germany

[21] Appl. No.: 36,238

[22] Filed: Mar. 24, 1993

[30] Foreign Application Priority Data

Apr. 16, 1992 [DE] Fed. Rep. of Germany ....... 4212809

[51] Int. Cl.$^5$ .......................................... A61B 17/22
[52] U.S. Cl. ..................................... 601/4; 128/660.03
[58] Field of Search ........ 128/24 AA, 24 EL, 660.03, 128/399

[56] References Cited

U.S. PATENT DOCUMENTS 5,065,741 11/1991 Uchiyama et al. ............. 128/24 EL

Primary Examiner—Ruth S. Smith
Attorney, Agent, or Firm—Hill, Steadman & Simpson

[57] ABSTRACT

A therapy apparatus for treating a patient with focused acoustic waves has a source of focused acoustic waves which converge in a focus zone, and a locating system for locating a therapeutically relevant region of the body of the patient. The locating system has a graphic display for displaying an image of the therapeutically relevant region (S). The apparatus also includes control and circuitry mixing a properly scaled contour (C) of the focus zone within the respective image defining a boundary within which the acoustic waves do not fall below a threshold with respect to an acoustic characteristic. The controls can be used to set the size of the contour directly, or to set the size with respect to one or more selected acoustic parameters.

11 Claims, 2 Drawing Sheets

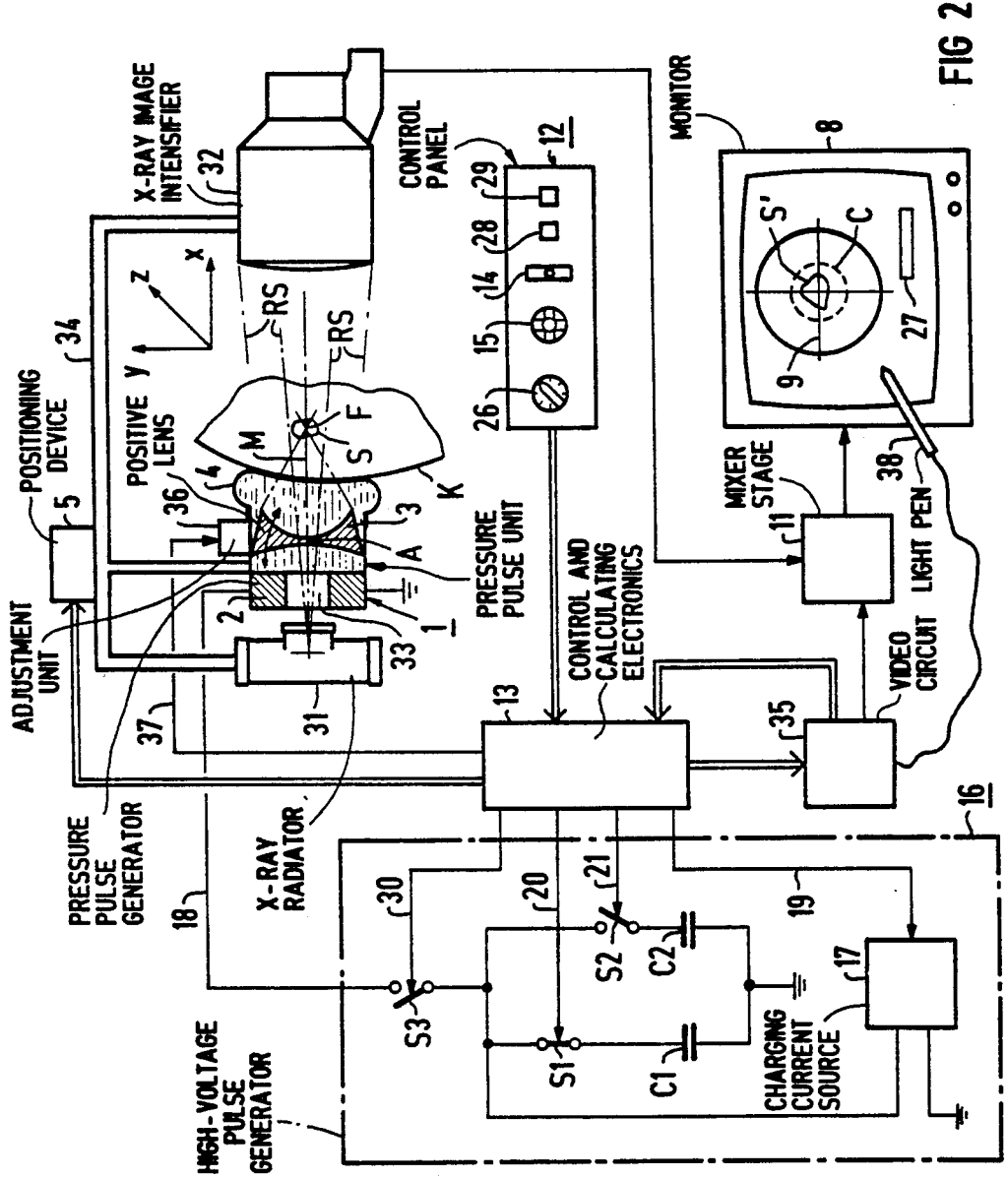

THERAPY APPARATUS FOR TREATING A SUBJECT WITH FOCUSED ACOUSTIC WAVES

BACKGROUND OF THE INVENTION

1. Field of the Invention

The present invention is directed to a therapy apparatus for treating a patient with focused acoustic waves, of the type having a source of focused acoustic waves that converge in a focus zone and a locating system for locating a therapeutically relevant region in the body of the patient, the locating system including a graphic display for an image of the therapeutically relevant region.

2. Description of the Prior Art

Acoustic wave systems are employed, for example, for treating stone pathologies (lithotripsy), tumors and bone pathologies (osteorestoration). One proceeds in the treatment that the therapeutically relevant region of the patient is first localized with the locating system, the source of acoustic waves and the body of the patient are then positioned relative to one another such that the therapeutically relevant region is located in the focus of the acoustic waves, and finally the therapeutically relevant region is charged with acoustic waves in the required way. The alignment of the source of acoustic waves and of the body of the patient relative to one another thereby ensues with the assistance of a mark mixed into the image on the graphic display, this mark indicating the position of the center of the focus zone of the acoustic waves in the image generated with the locating means. It has been shown that the most beneficial alignment of the source of acoustic waves and of the body of the patient relative to one another for producing a successful outcome to the therapy cannot always be found in this way.

In order to alleviate this situation, a therapy system disclosed in European Application 0 449 179 provides circuitry for mixing a contour of the focus zone being portrayed in the image, which contour defines a boundary outside of which the acoustic waves fall below a threshold with respect to an acoustic characteristic. The contour is displayed true to position and true to scale. The threshold is that threshold at which and above which the desired outcome of the therapy occurs. That region within which therapy can be successfully accomplished can thus be directly recognized in the image of the display. It is thus easily possible to align the source of acoustic waves and the body of the patient relative to one another such that the contour of the focus zone within which successful therapy can be accomplished and the therapeutically relevant region are aligned such relative to one another so that an optimally beneficial charging of the therapeutically relevant region with the focused acoustic waves is achieved. Such optimally beneficial charging means that the effect of the acoustic waves is essentially limited to the therapeutically relevant region and damage to the tissue surrounding this region is precluded to the greatest extent. It can be seen that the alignment of the source of acoustic waves and the body of the patient relative to one another found in this way will deviate in many cases from that alignment that is achieved in convention systems wherein only the center of the focus zone is marked.

SUMMARY OF THE INVENTION

It is an object of the present invention to provide a therapy system of the type initially described wherein an improved alignment of the source of acoustic waves and the body of the patient relative to one another, and a matching of the focus zone of the therapy system to the therapeutically relevant region to be treated, are possible.

This object is achieved in accordance with the principles of the present invention in a therapy system for treating a patient with focused acoustic waves having a source of focused acoustic waves which converge in a focus zone, locating means for locating a therapeutically relevant region of the body of the patient which includes graphic display means for displaying an image of the therapeutically relevant region, means for positionally correct and properly scaled mixing of that contour of the focus zone of the displayed image outside of which the acoustic waves fall below a threshold with respect to an acoustic characteristic, and setting means for setting the size of that region defined by the threshold contour for a given threshold by variation of a parameter. A good matching of that region within which therapy can be successfully accomplished to the therapeutically relevant region in question can ensue.

The setting means in a version of the invention can vary the peak pressure of the acoustic waves and/or the wavelength of the acoustic waves as the varied parameter. Alternatively or additionally, there is the possibility that the setting means vary the focusing effect of the focusing means as the varied parameter in devices wherein the source of focused acoustic waves includes a variable focusing means, such as the device disclosed in German OS 41 22 590. In order to enable a matching of the threshold to the current therapeutic requirements, it is provided in an embodiment of the invention that the threshold is adjustable. The contour of the focus zone of the displayed image, as used herein means that a different contour is mixed in the image dependent on the method used for the image acquistion by the locating system. For example, in the case of an x-ray locating system, a contour is mixed into the image which would arise if a three-dimensional region surrounding the center of the focus zone, within which the threshold is upwardly exceeded were to be imaged by x-radiation in its spatial position within the patient dependent on the alignment of the source of acoustic waves and the body of the patient relative to one another. In other words, it is as if this region were imaged as part of the body of the patient. If the image of the locating system is acquired by a tomographic method, for example an ultrasound B-scan, then the contour which the aforementioned three-dimensional region has in the imaged sectional plane is mixed into the image of the locating system. In a version of the invention, a value from the group of pressure (particularly peak pressure), energy density, and wavelength can be utilized as the acoustic characteristic dependent on the respective treatment method and treatment goal.

Another preferred embodiment of the invention includes means for prescribing a desired size (independent of parameters) of the contour of the focus zone with the respective image, and the setting means controls the selection of the size of this contour. The means for prescribing a desired size of the contour may be input means, for example a light pen, interacting with the graphic display. There is then the possibility of selecting a size of the contour of the focus zone specifically adapted to the size of the imaged, therapeutically relevant region in an extremely simple manner.

In another embodiment of the invention the setting means set the contour of the focus zone by varying of a plurality of parameters such that the maximum value of the critical acoustic characteristic of the acoustic waves exceeds the threshold as little as possible.

DESCRIPTION OF THE DRAWINGS

FIG. 2 is a schematic block diagram of an x-ray imaging apparatus constructed in accordance with the principles of the present invention in an embodiment employing tomographic imaging system in the locating system.

DESCRIPTION OF THE PREFERRED EMBODIMENTS

Figure 1:
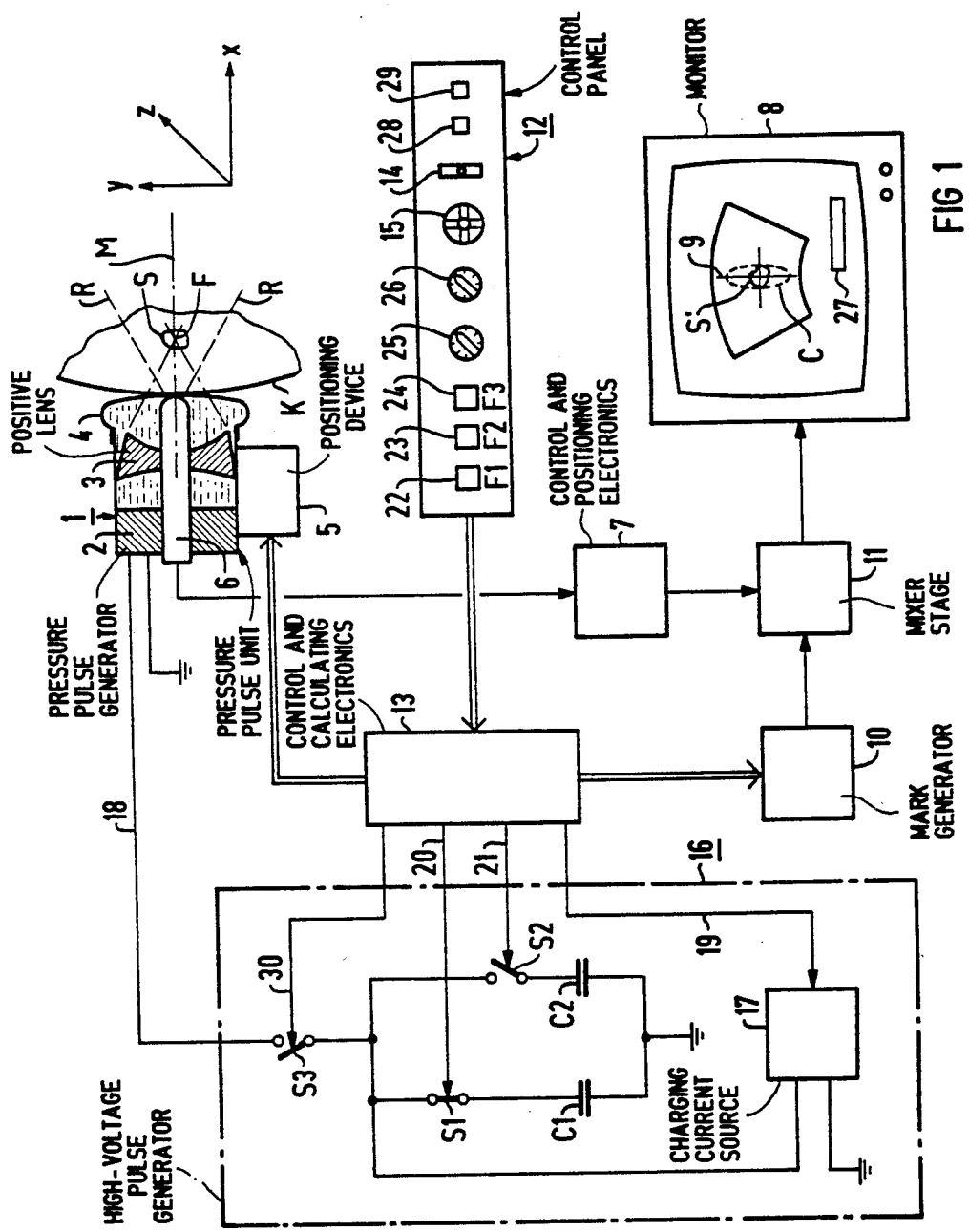
FIG. 1 is a schematic block diagram of an acoustic therapy apparatus constructed in accordance with the principles of the present invention in an embodiment employing tomographic imaging system in the locating system.

The therapy apparatus of FIG. 1 has an electromagnetic pressure pulse unit generally referenced 1 as its source of focused acoustic waves. Such pressure pulse unit are described in detail in U.S. Pat. No. 4,674,505 and European Application 0 188 750, and therefore the pressure pulse unit 1 is only schematically shown. The pressure pulse unit 1 contains an electromagnetic pressure pulse generator 2 that introduces planar pressure pulses into a liquid acoustic propagation medium, for example, water. These pressure pulses are focused onto a geometrical focus F with an acoustic positive lens 3 arranged in the propagation medium. The pressure pulse unit 1 also has a coupling means with which it can be acoustically coupled to the surface of the body K of a patient. In the exemplary embodiment being described herein, a flexible coupling cushion 4 is provided as the coupling means, which terminates the pressure pulse unit 1 liquid-tight, thus enclosing the acoustic propagation medium in the pressure pulse source 1.

In order to be able to align the pressure pulse source 1 relative to the body K of the patient such that a therapeutically relevant region S—for example, a calculus to be disintegrated such as a kidney stone or gall stone—is located in the region of the focus F, a schematically indicated motorized positioning device 5 is provided with which the pressure pulse unit 1 can be displaced in the direction of the three axes x, y and z of a Cartesian coordinate system.

This positioning procedure ensues with the assistance of a locating system employing tomographic imaging, in this case an ultrasound locating system which includes an ultrasound applicator 6, control and imaging electronics 7 connected thereto, and graphic display, for example a monitor 8, connected to the electronics 7. The ultrasound applicator 6, which is accepted in a central bore of the pressure pulse unit 1, is preferably a sector scanner arranged such that the sector-shaped slice of the body K (whose limiting lines are shown by dashed lines in FIG. 1 and referenced R) scanned by the applicator 6 contains the center axis M of the pressure pulse unit 1. The center axis M, on which the geometrical focus F also lies, preferably proceeds parallel to the x-axis. The z-axis then proceeds perpendicularly relative to the slice scanned with the ultrasound applicator 6. The ultrasound applicator 6 and the control and imaging electronics 7 are constructed and cooperate in a known way so that the monitor 8 displays an ultrasound B-image of the scanned slice of the body K. The position of the geometrical focus F in the ultrasound image is indicated with a graticule 9. The signal corresponding to the graticule 9 is generated with a mark generator 10 and is mixed into the output signal of the control and imaging electronics 7 in a mixing stage 11.

The therapy apparatus further includes a control panel 12 that is connected to control and calculating electronics 13 to which the positioning device 5 is in turn connected. For operating the positioning device 5, the control panel 12 has two control elements, namely a lever 14 and a joystick 15. The pressure pulse unit 1 can be displaced in both directions parallel to the z-axis with the lever 14. The position of the pressure pulse unit 1 at which the image S' of the therapeutically relevant region S has its maximum size in the ultrasound image is found by actuating the lever 14. By actuating the joystick 15, the pressure pulse unit 1 is subsequently displaced parallel to the x-axis and/or y-axis in the plane which contains its center axis M and proceeds parallel to the plane containing the x-axis and y-axis. This displacement takes place such that the graticule 9 lies approximately in the center of the image S' of the therapeutically relevant region S.

The therapy apparatus further includes a high-voltage pulse generator generally referenced 16 for driving the pressure pulse unit 1. The pulse generator 16 is connected via a high-voltage line to the pressure pulse generator 2 and is connected to the control and calculating electronics 13 via a plurality of control lines. The high-voltage pulse generator 16 contains a capacitor bank formed by two high-voltage capacitors C1 and C2 in the illustrated exemplary embodiment, the capacitance of the high-voltage capacitor C2 being larger than that of the high-voltage capacitor C1. Each of the high-voltage capacitors C1 and C2 has one terminal connected to ground. The other terminals of the high-voltage capacitors C1 and C2 can be connected to a charging current source 17 via respective switches S1 and S2. Dependent on whether only one of the switches S1 and S2, or both, are closed, only the high-voltage capacitor C1, only the high-voltage capacitor C2 or the parallel circuit of the high-voltage capacitors C1 and C2 is charged. The energy stored in the high-voltage capacitor C1 or C2, or in the parallel circuit can be discharged via a high-voltage cable 18 in the form of a pulse to the pressure pulse generator 16 for generating a pressure pulse, by closing a high-voltage switch S3.

The voltage of the charging current source 17, and thus the peak pressure of the pressure pulses generated by the pressure pulse unit 1, moreover, are adjustable. To this end, the charging current source 17 is in communication with the control and calculating electronics 13 via a control line 19. The actuation of the switches S1 and S2 as well as actuation of the high-voltage switch S3 also ensues with the control and calculating means 13 via control lines 20, 21 and 30.

The described fashioning of the high-voltage pulse generator 16 serves the purpose of permitting variation of the size of the region of the spatial focus zone around the geometrical focus F outside of which the generated pressure pulses fall below a threshold defined by an acoustic characteristic, namely with respect to their peak pressure. The term "peak pressure" as used herein means the highest value of the pressure that a pressure pulse reaches at a specific point of the acoustic field.

Therefore, the peak pressure is location-dependent. The maximum peak pressure is thus achieved in the center of the focus zone. The peak pressure, of course, decreases with increasing distance from the center of the focus zone. The acoustic field generated by the pressure pulse unit 1 can be described by isobars, i.e. lines or areas of identical pressure. The aforementioned region is also limited by an isobar, namely the threshold of the peak pressure. The variation of the size of this region occurs, for example, by varying the wavelength of the pressure pulses generated by the pressure pulse generator 2. This is achieved in a known way as described in European Application 0 387 858 by varying the capacitance of the capacitor bank of the high-voltage pulse generator 16. The wavelength of the pressure pulses generated with the pressure pulse generator 2 becomes shorter as the capacitance of the capacitor bank becomes lower. Since the focusing effect of the positive lens 3 is greater as the wavelength of the pressure pulses to be focused shortens, the aforementioned region becomes smaller as the capacitance of the capacitor bank is decreased. The control panel 12 has three keys 22 through 24 for selecting the size of the aforementioned region. When the key 22 (F1) is pressed, the control and calculating electronics 13 closes the switch S1 via the control line 20, and opens the switch S2 via the control line 21. Only the smallest capacitor C1 is thus charged by the charging current source 17, the consequence thereof being that the region has its smallest size after actuation of the key 22. When the key 24 (F3) is actuated, the control and calculating electronics 13 closes the switches S1 and S2 via the control lines 20 and 21, resulting charging of the parallel circuit of the high-voltage capacitors C1 and C2. In this case, the region has its maximum size. When the key 23 (F2) is actuated, the control and calculating electronics 13 opens the switch S1 via the control line 20, and closes the switch S2 via the control line 21. The high-voltage capacitor C2 is then active. Since the capacitance thereof is greater than that of the high-voltage capacitor C1 but is lower than the capacitance of the parallel circuit of the high-voltage capacitors C1 and C2, a medium size of the region results. The desired, maximum peak pressure of the pressure pulses is set with a rotary knob 25 on the control panel 12. Dependent on the position of the rotary knob 25 and dependent on which of the keys 22 through 24 was most recently actuated, i.e. dependent on what size of the region is set, the control and calculating unit 13—via the control line 19—sets the voltage supplied by the charging current source 17 such that the desired, maximum peak pressure of the pressure pulses is achieved. The control panel 12 has a further rotary knob 26 with which the threshold of the peak pressure limiting the said region can be selected.

Dependent on which size of the region is selected by actuating one of the keys 22 through 24, and dependent on which maximum peak pressure is selected with the rotary knob 25, and dependent on which threshold of the peak pressure is selected with the rotary knob 26, the control and calculating electronics 13 calculates that contour C of the region outside of which the set threshold of the peak pressure is downwardly transgressed. This calculation is made with reference to the slice of the body K of the patient portrayed in the ultrasound image. The control and calculating electronics 13 forwards corresponding data to the mark generator 10, which generates a signal resulting in a positionally correct and properly scaled mixing of the contour C into the ultrasound image when mixed with the output signal of the control and imaging electronics 7. In a field 27, the mark generator 10 also effects a mixing or gating of the set data in view of the maximum peak pressure and the threshold of the peak pressure. Mixing or gating of other relevant data, for example of the energy content of a pressure pulse, can be provided, in addition or alternatively.

For implementing a treatment, one proceeds by, as already described above, aligning the pressure pulse unit 1 and the body K of the patient relative to one another such that the image S' of the therapeutically relevant region S coincides with the graticule 9. Subsequently, a threshold of the peak pressure of the pressure pulses that is matched to the current treatment case is selected with the rotary knob 26. A maximum peak pressure that lies slightly above the threshold is then set with the rotary knob 25. Subsequently, a check is undertaken by actuating the keys 22 through 24 while observing the mixed-in contours C that arise upon actuation of the individual keys 22 through 24, to find the key 22 through 24 which produces the contour C matched best to the image S' of the therapeutically relevant region S. Proceeding from the best-matched contour C, the contour C is individually matched to the current treatment case by actuating the rotary knob 25 corresponding to the maximum peak pressure, whereby the contour C enlarges with increasing maximum peak pressure and becomes smaller with decreasing maximum peak pressure. It is clear that a maximum peak pressure cannot be set that falls below the set threshold of the peak pressure, since an effective treatment would otherwise not be possible. In the event such a setting is mistakenly selected, a corresponding indication ensues in the field 27. The most beneficial setting will normally be that setting wherein the image S' of the therapeutically relevant region S is just completely situated inside the contour C and the contour C is no larger than absolutely necessary. In order to be able to realize an optimally small contour C, it may be necessary to slightly correct the alignment of the pressure pulse unit 1 and the body K of the patient relative to one another found with reference to the graticule 9. It is assured in this case that the region of the focus zone wherein the threshold is reached or is downwardly transgressed is no larger than absolutely necessary. Of course, treatment cases can also occur wherein it is expedient to select the region of the focus zone substantially larger or smaller than the therapeutically relevant region, this being easily possible on the basis of the mixing or gating of the contour C and of the image S' of the therapeutically relevant region S.

When the optimum setting matched to the current treatment case has been found, charging of the therapeutically relevant region S with pressure pulses can begin. For this purpose, the control panel 12 has the two keys 28 and 29. When the key 28 is actuated, an individual pressure pulse is triggered. Upon actuation of the key 29, a periodic sequence of pressure pulses is triggered, this being interrupted given another actuation of the key 29. For triggering a pressure pulse, the control and calculating electronics 13 briefly closes the high-voltage switch S3 via the control line 30, so that the energy stored in the capacitor bank of the high-voltage pulse generator 16 discharges into the pressure pulse unit 1 or, more specifically, into the pressure pulse generator 2.

The exemplary embodiment of FIG. 2 coincides with that of FIG. 1 with regard to many components, for which reason identical or similar elements have the same reference characters.

A first difference relative to the embodiments set forth above is that the embodiment of FIG. 2 employs an x-ray locating system instead of an ultrasound locating system. This includes an x-ray radiator 31 and an oppositely disposed x-ray image intensifier 32. The arrangement is selected such that the central ray of the x-ray beam emanating from the x-ray radiator 31 proceeds at a right angle relative to the plane containing the y axis and the z axis. The pressure pulse unit 1, i.e. the pressure pulse generator 2 thereof and the positive lens 3 thereof, has a central region 33 that is transparent for x-radiation and through which the x-ray beam proceeds. The central ray of the x-ray beam preferably coincides with the center axis M of the pressure pulse unit 1. The pressure pulse unit 1, the x-ray radiator 31 and the x-ray image intensifier 32 are rigidly connected to one another with a schematically-indicated frame 34, and can be motor-adjusted with the positioning device 5 relative to the body K of a patient to be treated. Such adjustment takes place in the directions of the axes of the Cartesian coordinate system shown in FIG. 2. With reference to the x-ray image supplied by the x-ray locating system, the alignment can ensue such that the center axis M of the pressure pulse source, whose intersection with the input luminescent screen of the x-ray image intensifier 32 is marked in the x-ray image by a graticule 9, proceeds through the therapeutically relevant region S. This occurs with the assistance of the joystick 15 of the control panel 12 that is responsible for the adjustment in the direction of the y-axis and z-axis in the embodiment of FIG. 2. The alignment in the direction of the x-axis—the lever 14 is responsible for this adjustment motion in the case of FIG. 2—which is also required and which guarantees that the therapeutically relevant region S is situated in the region of the geometrical focus F ensues in a known way on the basis of additional information that can be acquired, for example, by a second x-ray locating system or by an additional ultrasound locating system (not shown).

The graticule 9 is mixed into the x-ray image with a video circuit 35 connected to the control and calculating electronics 13 and with the mixing stage 11. The video circuit 35 also generates the signals required for the mixing or gating of the contour C, whereby the contour C again indicates the boundary of the region of the focus zone outside of which the threshold of the peak pressure of the pressure pulses set with the rotary knob 26 of the control panel 12 is downwardly transgressed.

In addition to the measures undertaken in the embodiment of FIG. 1 for varying the size of the said region, the additional possibility is provided in the case of FIG. 2 of using a motorized adjustment mechanism 36 in order to pivot the positive lens 3 in the direction of the curved double-arrow around an axis A (which extends perpendicular to the plane of the drawing in the case of FIG. 2). The axis A intersects the center axis of the positive lens 3, which is identical to the center axis M of the pressure pulse unit 1, at a right angle. The focusing effect of the positive lens 3 can be influenced thereby in a known way.

After positioning the therapeutically relevant region S in the geometrical focus F of the pressure pulse source 1, the setting of the desired size of that region outside of which the set threshold of the peak pressure is downwardly transgressed ensues by entering an approximation of the desired contour of the region into the x-ray image with a light pen 38 connected to the video circuit 35. The video circuit 35 approximates this contour by a circle and forwards corresponding data with respect to the diameter of the region to the control and calculating electronics 13. The video circuit 35 also supplies an output signal to the mixer stage 11 that effects the mixing of a circular contour C, whose diameter corresponds to that of the circle approximated to the contour drawn on the picture screen with the light pen 38. The mixed-in contour C corresponds to that contour which would derive if the three-dimensional region surrounding the geometrical focus F within which the set threshold is reached or upwardly transgressed were imaged with the x-ray radiator 31 and the x-ray image intensifier 32.

The control and calculating electronics 13 first calculates the actual diameter of the region from the data supplied by the video circuit 35 and subsequently actuates the switches S1 and S2 such that the voltage supplied by the charging current source 17 is set such and, as warranted, the positive lens 3 is pivoted to an extent so that the region has the desired size and the maximum peak pressure of the pressure pulses is minimized. If a region having the desired size cannot be set for the given threshold, a corresponding message is displayed in the field 27 of the image of the monitor 8. The field 27, moreover, serves the other purposes already set forth.

There is also the possibility in the case of the embodiment of FIG. 2 to provide the control elements of FIG. 1 that serve the purpose of manually setting the size of the said region.

The programming of the control and calculating electronics 13 can be routinely undertaken by an engineer having acoustic knowledge and programming knowledge on the basis of his or her expertise in the field. This is also particularly true of the programming of the control and calculating electronics 13 in the case of the embodiment of FIG. 2 since the calculating procedures that are required for minimizing the peak pressure are a simple optimization problem that can be iteratively solved.

It is assumed in both exemplary embodiments that the body K of the patient remains at rest and the pressure pulse unit 1 together with the ultrasound applicator 6, or the x-ray radiator 31 and the x-ray image intensifier 32, are three-dimensionally adjusted. There is also the possibility of maintaining elements stationary and instead placing the patient on a three-dimensionally adjustable patient support table. Combined forms of these two approaches are possible.

In both exemplary embodiments, the energy density can also be utilized as the acoustic characteristic which defines the threshold. The variation of the size of that region outside of which the threshold of the energy density is downwardly transgressed then ensues by varying the (maximum) peak pressure and/or the wavelength of the shock waves.

A pressure pulse unit having an electromagnetic pressure pulse generator is shown in both of the exemplary embodiments. The therapy apparatus of the invention, however, can alternatively employ a pressure pulse unit having a pressure pulse generator operating on a different principle, for example piezoelectrically. Moreover, there is the possibility of providing other sources of acoustic waves, for example ultrasound waves, instead of a pressure pulse source. In this case, there is then the possibility of utilizing the therapy system for hyperthermic treatment methods. It is also clear that therapy systems constructed in accordance with the invention can be utilized not only for lithotripsy, as set forth in conjunction with the exemplary embodiments, but also for other medical purposes.

Focusing of the acoustic waves is not necessarily to be effected by means of acoustic lens means or by means of acoustic lens means alone, as in the case of described the examplary embodiments. Instead or additionally, for example, acoustic reflector means may be provided and/or a source of acoustic waves may be used which is shaped such, e.g. spherically, that the acoustic waves emanating from the source are already focused.

Although modifications and changes may be suggested by those skilled in the art, it is the intention of the inventor to embody within the patent warranted hereon all changes and modifications as reasonably and properly come within the scope of his contribution to the art.

I claim as my invention:

1. A therapy apparatus for treating a subject with focused acoustic waves comprising:
   means for generating acoustic waves exhibiting acoustic characteristics;
   means for focusing said acoustic waves to a focus zone;
   said means for generating and said means for focusing, in combination, having a plurality of parameters associated therewith which influence said acoustic characteristics of said acoustic waves;
   locating means for locating a therapeutically relevant region in a subject, including graphic display means for visually protraying an image of a portion of said subject containing said therapeutically relevant region;
   means for mixing a positionally correct and properly scaled contour into said image, said contour representing the boundary of a selected, displaced focus zone within said image outside of which said acoustic waves fall below a threshold of an acoustic characteristic; and
   setting means for setting the size of said selected displayed focus zone mixed into said image by varying at least one of said parameters.

2. A therapy apparatus as claimed in claim 1 wherein one of said parameters is a parameter defining the peak pressure of said acoustic waves, and wherein said setting means comprises means for varying said parameter defining the peak pressure of said acoustic waves.

3. A therapy apparatus as claimed in claim 1 wherein one of said parameters is a parameter defining the wavelength of said acoustic waves, and wherein said setting means comprises means for varying said parameter defining the wavelength of said acoustic waves.

4. A therapy apparatus as claimed in claim 1 wherein one of said parameters in the focusing effect of said means for focusing, and wherein said setting means comprises means for varying said focusing effect.

5. A therapy apparatus as claimed in claim 1 wherein said means for mixing includes means for setting a threshold of an acoustic characteristic selected from the group consisting of pressure, energy density and wavelength.

6. A therapy apparatus as claimed in claim 1 wherein said means for mixing includes means for setting a threshold of an acoustic characteristic selected from the group consisting of peak pressure, energy density and wavelength.

7. A therapy apparatus as claimed in claim 1 further comprising means for adjusting said threshold.

8. A therapy apparatus as claimed in claim 1 further comprising means for selecting a desired size of said contour of said focus zone within said image, and wherein said setting means includes means for setting a size of said contour corresponding to said desired size.

9. A therapy apparatus as claimed in claim 8 wherein said means for selecting a desired size of said contour within said image comprise input means for entering said desired size of said contour by interacting with said graphic display means.

10. A therapy apparatus as claimed in claim 1 wherein said setting means comprises means for setting the size of said focus zone mixed into said image by varying a plurality of said parameters.

11. A therapy apparatus as claimed in claim 10 wherein said setting means comprises means for setting the size of said focus zone mixed into said image by varying a plurality of said parameters with a maximum value of a selected acoustic characteristic exceeding said threshold as little as possible.

* * * * *